(12) United States Patent
Gao et al.

(10) Patent No.: US 9,568,410 B2
(45) Date of Patent: Feb. 14, 2017

(54) APPARATUS AND METHODS OF DETERMINING FLUID VISCOSITY

(75) Inventors: Li Gao, Katy, TX (US); Michael T. Pelletier, Houston, TX (US); Bob Engelman, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 625 days.

(21) Appl. No.: 13/637,256

(22) PCT Filed: Mar. 29, 2010

(86) PCT No.: PCT/US2010/029038
§ 371 (c)(1),
(2), (4) Date: Dec. 10, 2012

(87) PCT Pub. No.: WO2011/123093
PCT Pub. Date: Oct. 6, 2011

(65) Prior Publication Data
US 2013/0067995 A1 Mar. 21, 2013

(51) Int. Cl.
*G01N 11/16* (2006.01)
*E21B 49/08* (2006.01)
*G01N 9/00* (2006.01)

(52) U.S. Cl.
CPC ......... *G01N 11/16* (2013.01); *E21B 2049/085* (2013.01); *G01N 9/002* (2013.01)

(58) Field of Classification Search
CPC .................................................... G01N 11/16
USPC ...................... 73/54.01, 54.23, 54.24, 54.25, 54.26,73/54.27
See application file for complete search history.

(56) References Cited

U.S. PATENT DOCUMENTS

| | | | | |
|---|---|---|---|---|
| 4,524,610 A * | 6/1985 | Fitzgerald | .............. | G01N 9/002 73/32 A |
| 6,332,366 B1 * | 12/2001 | Wray | .................... | G01F 1/8418 73/861.356 |
| 6,334,356 B1 * | 1/2002 | Kita | ........................ | G01N 9/002 73/54.01 |
| 6,688,176 B2 * | 2/2004 | Storm, Jr. | ............. | G01F 1/8495 73/152.47 |
| 6,912,904 B2 | 7/2005 | Storm, Jr. et al. | | |
| 7,194,902 B1 | 3/2007 | Goodwin et al. | | |
| 7,222,671 B2 | 5/2007 | Caudwell et al. | | |

(Continued)

FOREIGN PATENT DOCUMENTS

| | | |
|---|---|---|
| CN | 1934426 A | 3/2007 |
| EP | 1306659 B1 | 6/2006 |

(Continued)

OTHER PUBLICATIONS

"Australian Application Serial No. 2010349753, Response filed Sep. 9, 2013 to Examiner Report mailed Nov. 12, 2012", 19 pgs.

(Continued)

*Primary Examiner* — Peter Macchiarolo
*Assistant Examiner* — Nathaniel Kolb

(57) ABSTRACT

Various embodiments include apparatus and methods of determining the viscosity of a fluid downhole in a well. A parameter of a response signal, obtained from driving a tube containing a fluid with an excitation signal for vibrating the tube, can be collected while maintaining the tube in a vibrating mode. The parameter can be evaluated to measure the viscosity of the fluid. In various embodiments, the fluid viscosity may be measured in-situ downhole in the well.

29 Claims, 7 Drawing Sheets

(56) References Cited

U.S. PATENT DOCUMENTS

| | | | |
|---|---|---|---|
| 7,284,449 B2 * | 10/2007 | Rieder | G01F 1/8409 73/861.356 |
| 7,296,484 B2 | 11/2007 | Rieder et al. | |
| 7,562,586 B2 | 7/2009 | Rieder et al. | |
| 7,574,898 B2 | 8/2009 | Harrison et al. | |
| 8,020,428 B2 * | 9/2011 | Snieder | G01N 9/002 73/32 A |
| 2002/0184940 A1 | 12/2002 | Storm, Jr. | G01F 1/8495 73/32 A |
| 2006/0086196 A1 * | 4/2006 | Rieder | G01F 1/8409 73/861.356 |
| 2007/0137313 A1 * | 6/2007 | Rieder | G01F 1/8409 73/861.357 |
| 2008/0245147 A1 * | 10/2008 | Snieder | G01N 9/002 73/32 A |
| 2008/0257036 A1 | 10/2008 | Chaudoreille | |

FOREIGN PATENT DOCUMENTS

| | | |
|---|---|---|
| EP | 1254352 B1 | 8/2006 |
| GB | 2236591 A | 4/1991 |
| GB | 2456034 A | 7/2009 |
| WO | WO-2006/094694 A1 | 9/2006 |
| WO | WO-2011123093 A1 | 10/2011 |

OTHER PUBLICATIONS

"Canadian Application Serial No. 2,766,252, Office Action mailed Aug. 13, 2013", 3 pgs.
"Canadian Application Serial No. 2,766,252, Response filed Feb. 3, 2014 to Office Action mailed Aug. 13, 2013", 22 pgs.
"Chinese Application Serial No. 201080027348.3, Response filed Feb. 21, 2014 to Office Action mailed Oct. 8, 2013", 18 pgs.
"European Application Serial No. 10712237.6, Office Action mailed Jan. 6, 2012"2 pgs.
"European Application Serial No. 10712237.6, Response filed Dec. 10, 2012 to Office Action mailed Jan. 6, 2012", 17 pgs.
Assael, M. J., et al., "An Absolute Vibrating-Wire Viscometer for Liquids at High Pressures", *International Journal of Thermophysics*, 12(2), (1991), 231-244.
Kandil, M., "The Development of a Vibrating Wire Viscometer and a Microwave Cavity Resonator for the Measurement of Viscosity, Dew Points, Density, and Liquid Volume Fracture at High Temperature and Pressure", Thesis, University of Canterbury, Christchurch, New Zealand, (2005), 189 pgs.
O'Keefe, M., et al., "In-Situ Density and Viscosity of Reservoir Fluids measured by Wireline Formation Testers", SPE 110364, *SPE Asia Pacific Oil and Gas Conference and Exhibition*, Oct. 30-Nov. 1, Jakarta, Indonesia, (2007), 1-15.
Tough, J. T., et al., "Vibrating Wire Viscometer", *The Review of Scientific Instruments*, 35(10), (1964), 1345-1348.
"Australian Application Serial No. 2010349753, Response filed Jun. 6, 2014 to Subsequent Examiners Report mailed Oct. 28, 2013", 17 pgs.
"Australian Application Serial No. 2010349753, Examiner Report mailed Nov. 12, 2012", 4 pgs.
"Chinese Application Serial No. 080027848.3, Office Action mailed Jan. 21, 2013", (w/ English Translation), 24 pgs.
"Chinese Application Serial No. 201080027848.3, Response filed Jun. 5, 2013 to Office Action mailed Jan. 21, 2013", (w/ English Translation of Claims), 21 pgs.
"International Application Serial No. PCT/US2010/029038, International Preliminary Report on Patentability mailed Oct. 11, 2012", 9 pgs.
"International Application Serial No. PCT/US2010/029038, Written Opinion mailed Dec. 10, 2010", 5 pgs.
"International Application Serial No. PCT/US2010/029038,Search Report mailed Dec. 10, 2010", 8 pgs.
"Australian Application Serial No. 2010349753, Subsequent Examiners Report mailed Oct. 18, 2013", 3 pgs.
"Chinese Application Serial No. 201080027848.3, Office Action mailed Oct. 8, 2013", (w/ English Translation), 19 pgs.
"Australian Application Serial No. 2010349753, Voluntary Amendment filed Oct. 2, 2014", 4 pgs.
"Canadian Application Serial No. 2,766,252, Response filed Oct. 1, 2014 to Office Action mailed Apr. 2, 2014", 34 pgs.
"Chinese Application Serial No. 201080027848.3, Response filed Aug. 8, 2014 to Office Action mailed May 27, 2014", (w/ English Translation of Claims), 15 pgs.
"Canadian Application Serial No. 2,766,252, Office Action mailed May 28, 2015", 4 pgs.
"European Application Serial No. 10712237.6, Examination Notification Art. 94(3) mailed Jul. 13, 2015", 6 pgs.
"Canadian Application Serial No. 2,766,252, Office Action mailed Apr. 2, 2014", 4 pgs.
"Chinese Application Serial No. 201080027848.3, Office Action mailed May 27, 2014", (w/ English Translation, 8 pgs.

* cited by examiner

```
┌─────────────────────────────────────────────────────────────┐
│ DETERMINE A PHASE DELAY BETWEEN A SIGNAL GENERATED FROM A   │
│ VIBRATING TUBE IN A WELL HOLE AND A DRIVE SIGNAL APPLIED TO │
│ THE VIBRATING TUBE                                          │
└─────────────────────────────────────────────────────────────┘
                                                         └─710

┌─────────────────────────────────────────────────────────────┐
│ DETERMINE THE VISCOSITY OF THE FLUID USING THE DETERMINED   │
│ PHASE DELAY                                                 │
└─────────────────────────────────────────────────────────────┘
                                                         └─720
```

FIG. 7

```
┌─────────────────────────────────────────────────────────────┐
│ CALCULATE THE DIFFERENCE BETWEEN A DETERMINED PHASE DELAY   │
│ AND A BASE DELAY, WHERE THE DIFFERENCE IS A DELTA PHASE DELAY│
└─────────────────────────────────────────────────────────────┘
                                                         └─810

┌─────────────────────────────────────────────────────────────┐
│ SELECT A VISCOSITY FROM A RELATIONSHIP OF VISCOSITY AS A    │
│ FUNCTION OF DELTA PHASE DELAY                               │
└─────────────────────────────────────────────────────────────┘
                                                         └─820
```

FIG. 8

APPARATUS AND METHODS OF DETERMINING FLUID VISCOSITY

RELATED APPLICATIONS

This application is a U.S. National Stage Filing under 35 U.S.C. 371 from International Application No. PCT/US2010/029038, filed on Mar. 29, 2010, and published as WO 2011/123093 A1 Oct. 6, 2011; which application and publication are incorporated herein by reference in their entirety.

TECHNICAL FIELD

The present invention relates generally to systems capable of making measurements in a well.

BACKGROUND

In drilling wells for oil and gas exploration, understanding the structure and properties of the geological formation surrounding a borehole provides information to aid such exploration. However, the environment in which the drilling tools operate is at significant distances below the surface and measurements to manage operation of such equipment are made at these locations. Further, the usefulness of such measurements may be related to the precision or quality of the information derived from such measurements.

BRIEF DESCRIPTION OF THE DRAWINGS

Embodiments of the invention are illustrated by way of example and not limitation in the figures of the accompanying drawings in which:

FIG. 7 shows features of an example embodiment of a method to measure viscosity downhole in a well using a drive signal that vibrates a tube.

FIG. 8 shows features of an example embodiment of a method to determine viscosity using a determined phase delay between a response signal and its corresponding drive signal.

DETAILED DESCRIPTION

The following detailed description refers to the accompanying drawings that show, by way of illustration, various embodiments of the invention. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

Figure 1:
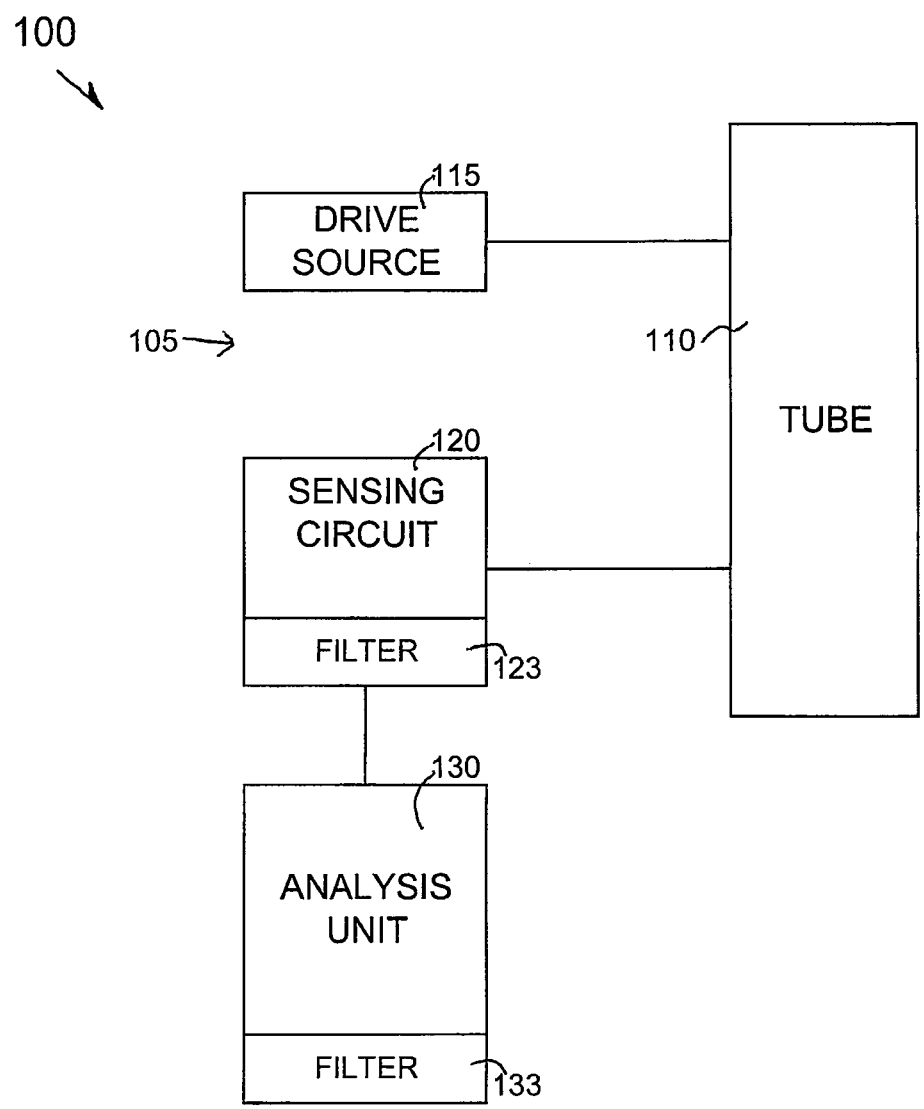
FIG. 1 shows an embodiment of an apparatus having a sensor device to measure fluid viscosity in-situ downhole in a well, according to various embodiments.

FIG. 1 shows an embodiment of an apparatus 100 having a sensor device 105 to measure fluid viscosity in-situ downhole in a well. Sensor device 105 includes a tube 110 to contain fluid extracted from the well, a drive source 115 to generate a drive signal to vibrate the tube, and a sensing circuit 120 to generate a response signal representing a response of the tube to the drive signal. The drive signal may include a base signal at a resonant frequency for apparatus 100. Tube 110 is a structure that into which a fluid may be directed and held for measurement of a property of the fluid. The housing for sensor device 105 can include flow control components, such as a pump, to control collection of the fluid within tube 110 for measurement of fluid properties including determination of the viscosity of the fluid.

Apparatus 100 includes an analysis unit 130 to determine a parameter associated with the response signal, where the viscosity of the fluid brought into tube 110 can be determined using the parameter. The parameter can be obtained from the response signal generated in response to the drive signal applied to the tube such that the response signal is captured as the vibrating tube is being driven, that is, acquisition of the parameter associated the response signal occurs with the tube maintained in a vibrating mode. The parameter can include an attenuation in the response signal, a phase delay between the drive signal and the response signal, or other characteristic correlated to the response signal from which the viscosity of the fluid in tube 110 can be calculated. Analysis unit 130 can determine the viscosity of the fluid using the parameter determined from the response of tube 110 to a drive signal.

Drive source 115 includes a circuit to generate a drive signal to excite tube 110 to vibration such that a response signal to such vibration can be used to measure one or more properties of a fluid in tube 110. In various embodiments, drive source 115 includes a circuit to generate a drive signal having a waveform containing a base signal modulated by a square wave having a low frequency relative to the frequency of the base signal. The base signal may be at a resonant frequency. The response of tube 110, containing fluid from the well, to the square wave modulated drive signal can be filtered to determine an attenuation factor that occurs when tube 110 is vibrated by the base signal with the square wave during its low amplitude portion of its cycle. Such filtering can be realized with a low pass filter 123 in sensing circuit 120 or with a low pass filter 133 in analysis unit 130.

The difference between the attenuation measured with tube 110 containing fluid and the attenuation measured with respect to tube 110 without containing fluid can be used to measure viscosity. The attenuation measured with tube 110 without containing fluid provides a base attenuation that does not include the effects of the viscosity of the fluid being measured. The viscosity can be measured by considering a correlation between viscosity and a difference between the attenuation measured and the base attenuation. This difference in attenuation can be referred to as a delta attenuation. Analysis unit 130 can include a database containing delta attenuation factors for known viscosities. Measurement of a delta attenuation of a fluid under examination in tube 110 can be correlated with the information in the database to provide a measurement of the viscosity of the fluid.

Other drive signals can be generated. In various embodiments, the circuit of drive source 115 can generate a base sinusoidal signal modulated by a lower frequency sinusoidal signal. The base sinusoidal signal may be generated at a resonant frequency for apparatus 100. The response of tube 110 containing fluid from the well to this drive signal can be filtered to determine a phase delay between the drive signal and the response signal from vibrating tube 110. Such filtering can be realized with a low pass filter 123 in sensing circuit 120 or with a low pass filter 133 in analysis unit 130. Other drive signals can be generated in which the response signal is not filtered. Such drive signals can include a sinusoidal signal without a superimposed modulating signal, where a phase delay is obtained by directly comparing the phase delay between the drive signal and the response signal. The difference between the phase delay measured with tube 110 containing fluid and the phase delay measured with tube 110 without containing fluid can be used to measure viscosity.

Using a modulated or an un-modulated sinusoidal drive signal, the phase delay measured with tube 110 without containing fluid provides a base phase delay that does not include the effects of the viscosity of the fluid being measured. The viscosity can be measured by considering a correlation between viscosity and a difference between the phase delay measured and the base phase delay. This difference in phase delay can be referred to as a delta phase delay. Analysis unit 130 can include a database containing delta phase delays for known viscosities. Measurement of a delta phase delay of a fluid under examination in tube 110 can be correlated with the information in the database to provide a measurement of the viscosity of the fluid.

Analysis unit 130 can include a machine-readable medium that stores instructions, which when performed by apparatus 100, cause apparatus 100 to perform various operations. Such operations can include determining a parameter in the response signal from tube 110 vibrating in the well, where tube 110 contains fluid from the well. Such parameter can include, but is not limited to, an attenuation in the response signal from tube 110 vibrating in the well or a phase delay between the drive signal and the response signal. The response signal, with respect to the drive signal applied to tube 110, can be generated such that the parameter can be collected as vibrating tube 110 is being driven. The viscosity of the fluid can be determined using the determined parameter. The instructions can include instructions to determine the viscosity of the fluid using the determined parameter. Such instructions can include determining a delta of the parameter as a difference in value between a base value of the parameter and a determined value of the parameter and selecting a viscosity from a relationship of viscosity as a function of the delta of the parameter evaluated at the determined delta of the parameter from a particular measurement of the parameter.

Analysis unit 130 can be integrated in a housing with sensor device 105. Alternatively, analysis unit 130 may be realized as a separate unit from sensor device 105. Analysis unit 130 as a separate unit can be operated at the surface to a well, while sensor device 105 operates downhole in the well, where the analysis unit 130 and the sensor device 105 are communicatively coupled. Analysis unit 130 as a separate unit can be operated downhole in the well as sensor device 105 operates downhole in the well. Sensor device 105 and/or analysis unit 130 can be arranged in a wireline-logging configuration, a logging-while-drilling (LWD) configuration, or a measuring-while-drilling (MWD) configuration.

In various embodiments, sensor device 105 can be realized utilizing an existing vibrating tube density sensor, where the electronics are modified to provide sensor device 105 and analysis unit 130. A typical fluid density sensor is based on the measurement of resonance of a vibrating tube containing fluid. In such fluid density sensors, the resonance frequency is measured with a feedback circuit as part of the sensor electronics. The output of the circuit is at the resonance frequency. The displacement of a sensing magnet of the fluid density sensor can be described by $y(t)=A\cos(\omega t+\phi)$. When viscosity of the fluid is considered, there will be additional energy loss in the resonant state of the sensor. For any resonance system, the energy loss can be quantified by its quality factor Q. The quality factor Q is related to the ratio of energy stored to energy dissipated per cycle.

After driving the vibrating tube with a constant force for a period of time, when the driving force is turned off, the amplitude of the vibration will be attenuated. Thus, the displacement of the sensing magnet in this case will be described by $y(t)=Ae^{-\beta t}\cos(\omega t+\phi)$. By monitoring the rate of attenuation, β, also referred to as an attenuation coefficient, the quality factor Q can be determined. With the knowledge of Q, the viscosity can be inferred.

Unfortunately, it may not be desirable to turn the driving force to the fluid density sensor completely off. Experiments have shown that once the tube of the fluid density sensor stops vibrating, often it is difficult to restart it automatically. Instead, it is desirable to maintain a non-zero vibration amplitude at all times while measuring the quality factor.

In various embodiments, drive signals to a tube containing fluid from a well are used that maintain a non-zero vibration amplitude at all times while measuring the quality factor for measuring viscosity. With the modulated drive signal maintaining a non-zero vibration amplitude, the tube, similar or identical to tube 110 of FIG. 1, does not stop vibrating.

Figure 2:
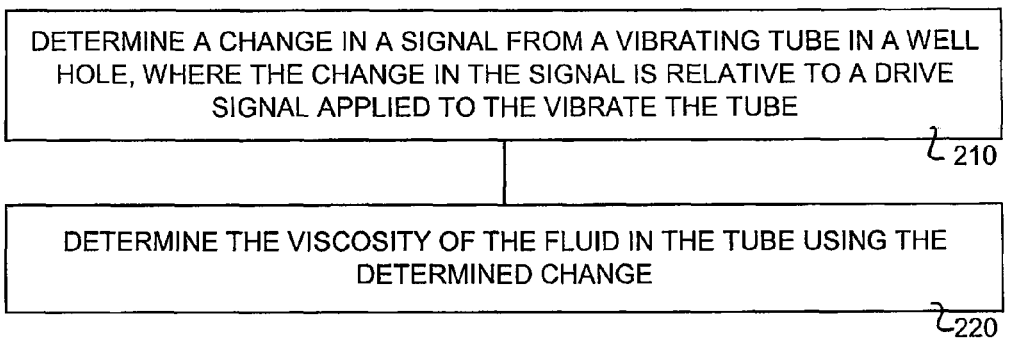
FIG. 2 shows features of an embodiment of a method to measure viscosity downhole in a well, according to various embodiments.

FIG. 2 shows features of an embodiment of a method to measure viscosity downhole in a well. At 210, a change in a signal from a vibrating tube in a well is determined, where the change in the signal is relative to a drive signal applied to vibrate the tube. The change can be a parameter associated with the response signal. The vibrating tube contains fluid from the well, where the fluid is under measurement to determine its viscosity. The signal generated in response to the drive signal applied to the vibrating tube is a waveform generated such that change of the signal occurs as the vibrating tube is being driven. At 220, the viscosity of the fluid is determined using the determined change. The viscosity of the fluid can be determined using the determined change by determining a delta change as a difference in value between a base change and the determined change and selecting a viscosity from a relationship of viscosity as a function of delta change evaluated at the determined delta change. The change can be an attenuation, a phase delay between the response signal and the drive signal, or some other measurable parameter from a signal that can be used to measure viscosity.

Figure 3A:
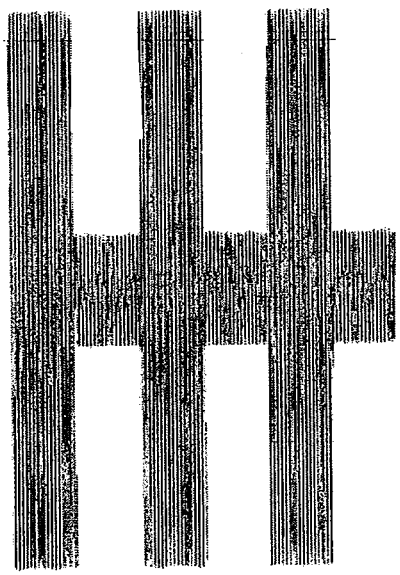
FIG. 3A shows a drive signal having a waveform of a base drive signal modulated with a low frequency square wave that can be implemented to vibrate a tube containing fluid downhole in a well, according to various embodiments.
Figure 3B:
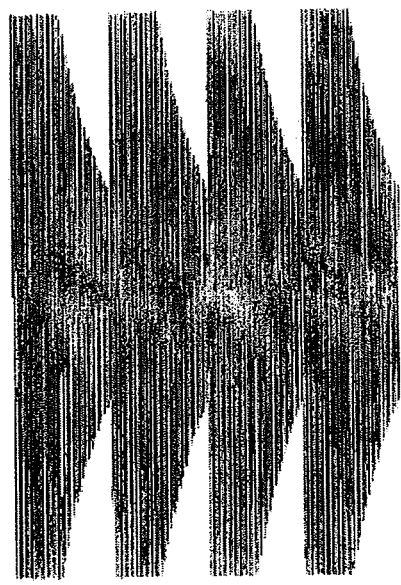
FIG. 3B shows a response to the drive signal of FIG. 3A, according to various embodiments.

FIG. 3A shows a drive signal having a waveform of a base drive signal modulated with a low frequency square wave that can be implemented to vibrate a tube containing fluid downhole in a well, according to various embodiments. This drive signal can be applied in apparatus 110 of FIG. 1 or used in a vibrating tube density sensor with modified electronics to apply the drive signal, sense the response signal, and make a determination of the viscosity of the fluid. In various embodiments, a vibrating tube density sensor is used as a viscosity sensor with no structural changes, but with modification to some measurement electronics. With the drive signal maintaining a non-zero vibration amplitude, the tube does not stop vibrating. The time Q factor can be calculated from the attenuated portion of the waveform after removing the high vibrating frequency with a low-pass filter. Use of a base driving signal modulated with a low frequency square wave allows implementation of time stacking to enhance signal-to-noise ratio in the attenuated part of the data. FIG. 3B shows the response to the drive signal showing attenuation during the portions of time that the amplitude of the square wave is at its low amplitude.

Figure 4:
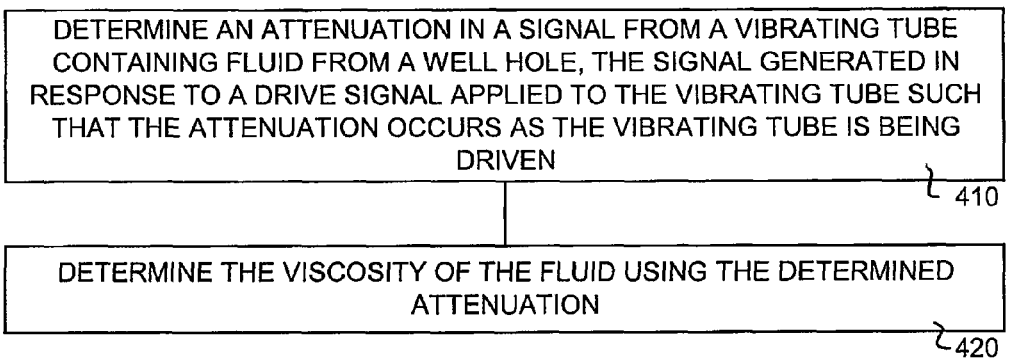
FIG. 4 shows features of an example embodiment of a method to measure viscosity downhole in a well using a base drive signal modulated by a square wave.

FIG. 4 shows features of an example embodiment of a method to measure viscosity downhole in a well using a base drive signal modulated by a square wave. The drive signal may be implemented as the drive signal shown in FIG. 3. However, the various parameters, such as amplitude and frequency, for such a signal can be adjusted according to its application. At 410, an attenuation in a signal from a vibrating tube in a well is determined. The vibrating tube contains fluid from the well, where the viscosity of the fluid is the subject of the measurement. The signal generated in response to the drive signal applied to the vibrating tube is a waveform generated such that the attenuation occurs as the vibrating tube is being driven, that is, a non-zero excitation is continually applied to the vibrating tube during measurement of the attenuation. At 420, the viscosity of the fluid is determined using the determined attenuation.

Figure 5:
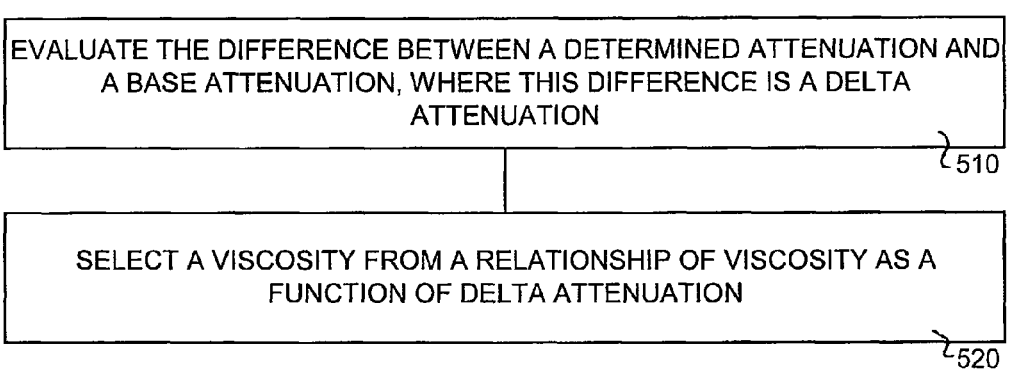
FIG. 5 shows features of an example embodiment of a method to determine viscosity using a determined attenuation of a response signal.

FIG. 5 shows features of an example embodiment of a method to determine viscosity using a determined attenuation of a response signal. At 510, the difference between a determined attenuation and a base attenuation is evaluated, where this difference is a delta attenuation. At 520, a viscosity is selected from a relationship of viscosity as a function of delta attenuation, that is, viscosity as a function of the difference between a determined attenuation with the tube containing the fluid under measurement and a base attenuation.

In various embodiments, the base attenuation and relationship of viscosity with respect to a delta attenuation can be generated through an iterative process. This iterative process can be conducted in advance of measuring a fluid viscosity in the well, or at the time of the measurement. The iterative process can be conducted for each type of drive signal used. In the iterative process, the sensor is driven with a signal without fluid in the vibrating tube. The signal may be a base drive signal modulated with a low frequency square wave. The response of the vibrating tube is measured. The attenuation coefficient, $\beta_o$, from the low amplitude portion of the square is determined. With the tube vibrated without containing a fluid, this measurement quantifies all energy losses in the sensor other than that from viscosity. The measured attenuation coefficient, $\beta_o$, becomes a base attenuation coefficient.

The measurement of an attenuation coefficient, $\beta$, is repeated with a known fluid in the tube, where the fluid has a known viscosity, $\eta$. This provides a mapping of the determined value of the attenuation coefficient $\beta$ to the known $\eta$ value. The measurement of attenuation coefficients is repeated with different fluids in the tube, where the different fluids have different known viscosities $\eta$. Each measurement provides an attenuation coefficient $\beta$ for each viscosity $\eta$. This mapping of $\eta$ to $\beta$ ($\beta$ to $\eta$) includes energy losses in the sensor in addition to viscosity.

The viscosity can be mapped to its associated attenuation property for the sensor by calculating the difference between the measured attenuation coefficient and the base attenuation coefficient for the known fluid in the tube. The result, a delta attenuation coefficient, $\Delta\beta$, is given by $\Delta\beta=\beta-\beta_o$. A delta coefficient can be calculated for each of the different fluids with respect to their different known viscosities.

The delta attenuation coefficients and/or attenuation coefficients can be stored in a database correlated to the known viscosities. This establishes a database of a correlation function $\Delta\beta=F(\eta)$. After establishing the correlation of delta attenuation coefficients with known viscosity in the database, upon measuring a delta attenuation coefficient for a fluid in the vibrating tube, the database can be accessed to determine the nearest delta attenuation coefficients greater than and less than the measured delta attenuation coefficient and their corresponding viscosities. From these values, the viscosity for the measured delta attenuation coefficient can be interpolated. In addition to a database having a discrete function with a finite number of delta attenuation coefficients and their corresponding viscosities, these finite number of data points can be used to generate a curve for the function $\Delta\beta=F(\eta)$ using one or more curve fitting techniques.

With the delta attention coefficients and known viscosities stored in the database, a mechanism is provided for assigning a viscosity to a fluid from downhole in a well measured in a vibrating tube. A relationship of viscosity as a function of delta attenuation can be generated. This function may be generated as a curve using various curve fitting techniques. Further, the correlation function $\Delta\beta=F(\eta)$ can be inverted to obtain the inverse function $\eta=F^{-1}(\Delta\beta)$. The determined relationship of viscosity as a function of delta attenuation coefficient for a given drive signal exciting a given tube can be used to identify the value of the viscosity of fluid being measured in the tube. The vibrating tube may be realized as a tube of a fluid density sensor.

Figure 6:
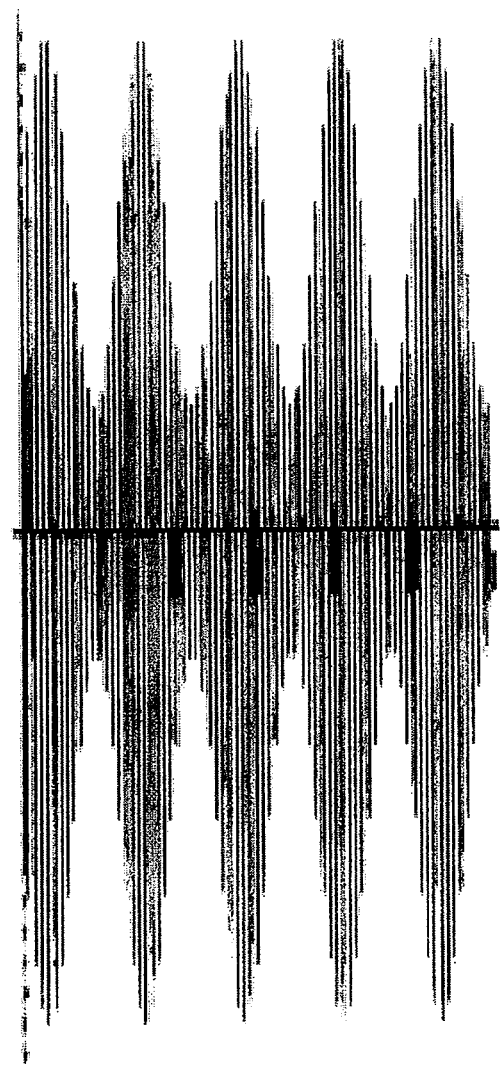
FIG. 6 shows a drive signal having a waveform of a base sinusoidal drive signal modulated with a sinusoidal low frequency wave that can be implemented to vibrate a tube containing fluid downhole in a well, according to various embodiments.

FIG. 6 shows a drive signal having a waveform of a base sinusoidal drive signal modulated with a sinusoidal low frequency wave that can be implemented to vibrate a tube containing fluid downhole in a well, according to various embodiments. The energy loss due to viscosity will induce a phase delay $\Delta\phi$ in the modulated response. The response to the drive signal can be evaluated after subjecting the response to low-pass filtering. A phase delay between the drive signal and the filtered response signal can be used to measure viscosity of the fluid in the vibrating tube downhole in a well. Alternatively, a sinusoidal drive signal without a low frequency modulation can be used. In this case, the phase delay between the drive signal and the response signal without any filtering can be directly compared to obtain the phase delay.

FIG. 7 shows features of an example embodiment of a method to measure viscosity downhole in a well using a drive signal that vibrates a tube. At 710, a phase delay between a signal generated from a vibrating tube in a well and a drive signal applied to the vibrating tube is determined. The vibrating tube contains a fluid from the well to be evaluated for its viscosity. The signal generated in response to the drive signal applied to the vibrating tube is a waveform such that measurement of the phase delay occurs as the vibrating tube is being driven, that is, a non-zero excitation is continually applied to the vibrating tube during measurement of the phase delay. The drive signal may be realized as a base sinusoidal drive signal modulated with a sinusoidal low frequency wave, where the corresponding evaluated response is a filtered response. The drive signal may be realized as a base sinusoidal drive signal without low frequency modulation, where the corresponding evaluated response is an unfiltered response. At 720, the viscosity of the fluid using the determined phase delay is determined.

FIG. 8 shows features of an example embodiment of a method to determine viscosity using a determined phase delay between a response signal and its corresponding drive signal. At 810, the difference between a determined phase delay and a base delay is calculated, where this difference is a delta phase delay. At 820, a viscosity is selected from a relationship of viscosity as a function of delta phase delay, that is, viscosity as a function of the difference between a determined phase delay with the tube containing the fluid under measurement and a base phase delay.

In various embodiments, the base phase delay and relationship of viscosity with respect to a delta phase delay can be generated through an iterative process. This iterative process can be conducted in advance of measuring a fluid viscosity in the well, or at the time of the measurement. The iterative process can be conducted for each type of drive signal used. In the iterative process, the sensor is driven with a drive signal without fluid in the vibrating tube. The drive signal may be a base sinusoidal drive signal modulated with a sinusoidal low frequency wave. Alternatively, the drive signal may be a base sinusoidal drive signal without a low frequency modulation. In this case, the phase delay is obtained by directly comparing the phase delay between the driver signal and the response signal without low-pass filtering. The response of the vibrating tube is measured. The phase delay, $\Delta\phi_0$, between the low frequency drive signal and the response after low-pass filtering is determined. With the tube vibrated without containing a fluid, this measurement gives the phase delay due to all energy losses in the sensor other than that from viscosity. The measured phase delay, $\Delta\phi_0$, becomes a base phase delay.

The measurement of a phase delay, $\Delta\phi$, between the drive signal and response signal is repeated with a known fluid in the tube, where the fluid has a known viscosity, $\eta$. This provides a mapping of the determined value of the phase delay, $\Delta\phi$, to the known $\eta$ value. The measurement of phase delays is repeated with different fluids in the tube, where the different fluids have different known viscosities $\eta$. Each measurement provides a phase delay $\Delta\phi$ for each viscosity $\eta$. This mapping of $\eta$ to $\Delta\phi$ ($\Delta\phi$ to $\eta$) includes energy losses in the sensor in addition to viscosity.

The viscosity can be mapped to its associated phase delay property for the sensor by calculating the difference between the measured phase delay and the base phase delay for the known fluid in the tube. The result, a delta phase delay, $\delta$, is given by $\delta = \Delta\phi - \Delta\phi_0$. A delta phase delay can be calculated for each of the different fluids with respect to their different known viscosities.

The delta phase delays and/or phase delays can be stored in a database correlated to the known viscosities. This establishes a database of a correlation function $\delta = G(\eta)$. After establishing the correlation of delta phase delays with known viscosity in the database, upon measuring a delta phase delay for a fluid in the vibrating tube, the database can be accessed to determine the nearest delta phase delay greater than and less than the measured delta phase delay and their corresponding viscosities. From these values, the viscosity for the measured delta phase delay can be interpolated. In addition to a database having a discrete function with a finite number of delta phase delays and their corresponding viscosities, these finite number of data points can be used to generate a curve for the function $\delta = G(\eta)$ using various curve fitting techniques.

With the delta phase delays and known viscosities stored in the database, a mechanism is provided for assigning a viscosity to a fluid from downhole in a well measured in a vibrating tube. A relationship of viscosity as a function of delta phase delay can be generated. This function may be generated as a curve using various curve fitting techniques. Further, the correlation function $\delta = G(\eta)$ can be inverted to obtain the inverse function $\eta = G^{-1}(\delta)$. The determined relationship of viscosity as a function of delta phase delay for a given drive signal exciting a given tube can be used to identify the value of the viscosity of fluid being measured in the tube. The vibrating tube may be realized as a tube of a fluid density sensor.

Various components of a downhole fluid viscosity measurement tool having a tube capable of vibrating that operates to take measurements while maintaining the tube in a vibrating mode, as described herein or in a similar manner, can be realized in hardware implementations, software implementations, and combinations of hardware and software implementations. These implementations may include a machine-readable medium having machine-executable instructions, such as a computer-readable medium having computer-executable instructions, for operating the system to excite the tube to a vibrating mode, collect response signals related to the drive signals that excite the tube while maintaining the tube in the vibrating mode, and determine viscosity of a fluid in the vibrating tube. The machine-readable medium can also store parameters used in execution of the instructions and can also store results from execution of the instructions. The form of machine-readable medium is not limited to any one type of machine-readable medium, but can be any machine-readable medium. For example, machine-readable medium can include a data storage medium that can be implemented in a housing disposed in a collar of a drill string or in a wireline configuration and/or in a system control center.

Figure 9:
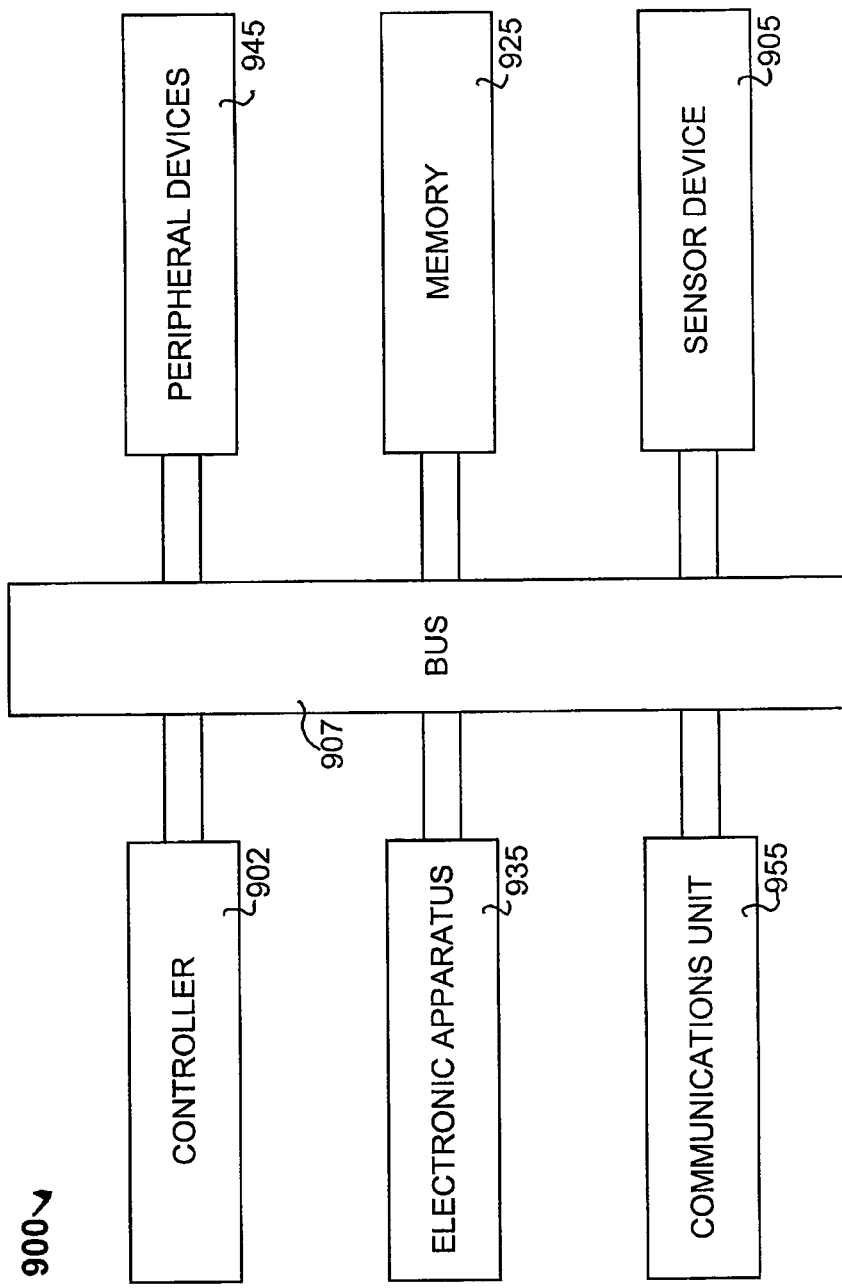
FIG. 9 depicts a block diagram of features of an embodiment of a system having components to measure viscosity downhole in a well using a drive signal that vibrates a tube.

FIG. 9 depicts a block diagram of features of an embodiment of a system 900 having a controller 902, a memory 925, an electronic apparatus 935, a communications unit 955, and sensor device 905 having a vibrating tube for measuring viscosity of a fluid downhole in a well. Controller 902, memory 925, and communications unit 955 can be arranged to operate sensor device 905. Sensor device 905 can be realized in accordance with fluid viscosity measurement tools described herein. Electronic apparatus 935 can include components, such as components similar to or identical to analysis unit 130 of FIG. 1, operable to assist in analyzing a signal generated in response to excitation of the vibrating tube. Communications unit 955 can include downhole communications in a drilling operation. Such downhole communications can include a telemetry system.

System 900 can also include a bus 907, where bus 907 provides electrical conductivity among the components of system 900. Bus 907 can include an address bus, a data bus, and a control bus, each independently configured. Bus 907 can also use common conductive lines for providing one or more of address, data, or control, the use of which is regulated by controller 902. Bus 907 can be configured such that the components of system 900 are distributed. Such distribution can be arranged between downhole components such as a vibration tube with excitation circuits and surface components such as components to analyze signals sensed from the vibrating tube. Alternatively, the components can be co-located such as on one or more collars of a drill string or on a wireline structure.

In various embodiments, peripheral devices 945 include displays, additional storage memory, and/or other control devices that may operate in conjunction with controller 902 and/or memory 925. In an embodiment, controller 902 is a processor. A peripheral device arranged as a display can be used with instructions stored in memory 925 to implement a user interface to manage the operation of sensor device 905 in system 900 and distributed among the components of system 900.

Figure 10:
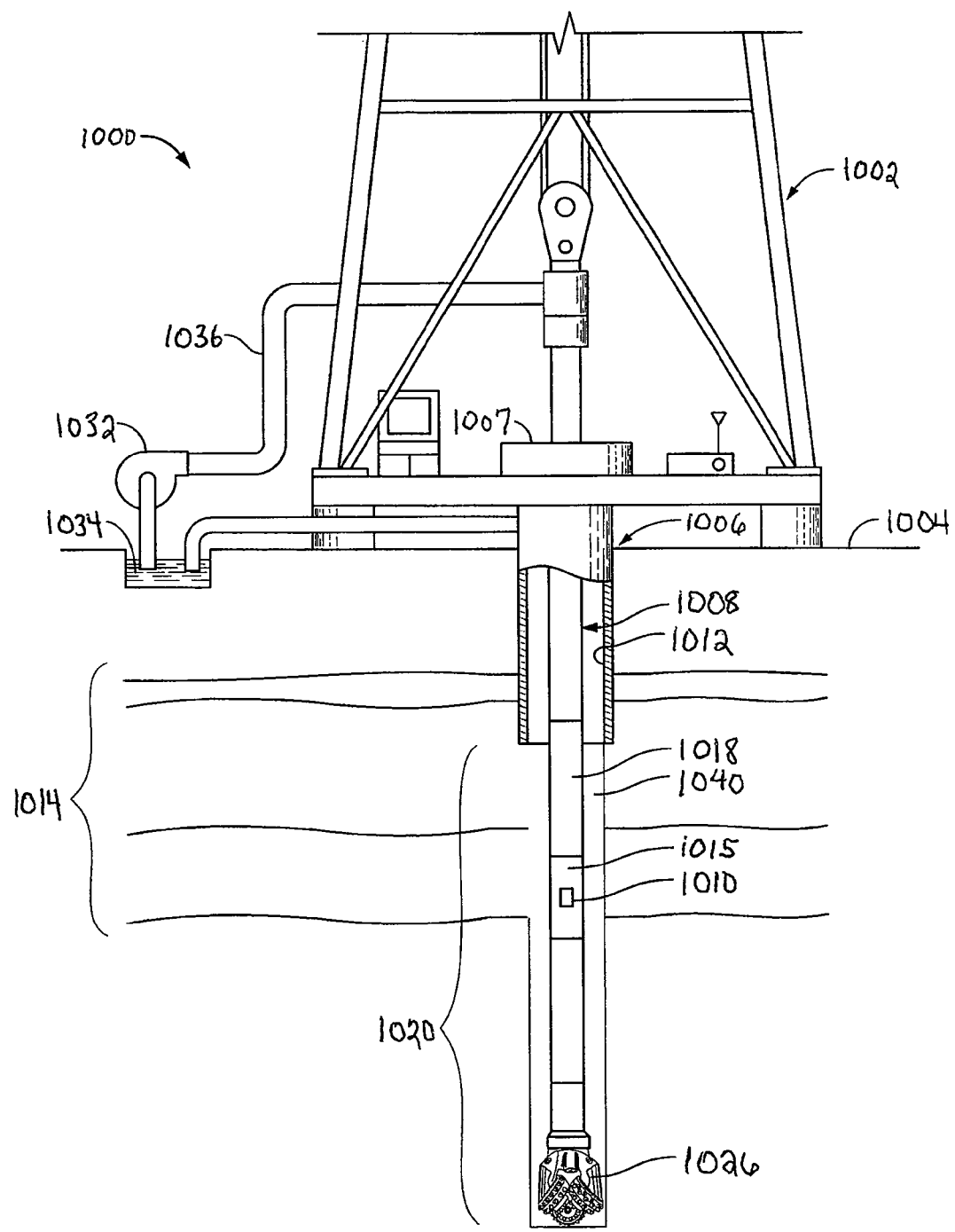
FIG. 10 depicts an embodiment of a system at a drilling site, according to various embodiments.

FIG. 10 depicts an embodiment of a system 1000 at a drilling site, where system 1000 includes a measurement tool and electronics to determine fluid viscosity downhole in a well. System 1000 can include a drilling rig 1002 located at a surface 1004 of a well 1006 and a string of drill pipes, that is drill string 1008, connected together so as to form a drilling string that is lowered through a rotary table 1007 into a wellbore or borehole 1012. The drilling rig 1002 may provide support for drill string 1008. The drill string 1008 may operate to penetrate rotary table 1007 for drilling a borehole 1012 through subsurface formations 1014. The drill string 1008 may include drill pipe 1018 and a bottom hole assembly 1020 located at the lower portion of the drill pipe 1018.

The bottom hole assembly 1020 may include drill collar 1015, sensor 1010 attached to drill collar 1015, and a drill bit 1026. The drill bit 1026 may operate to create a borehole 1012 by penetrating the surface 1004 and subsurface formations 1014.

During drilling operations, the drill string 1008 may be rotated by the rotary table 1007. In addition to, or alternatively, the bottom hole assembly 1020 may also be rotated by a motor (e.g., a mud motor) that is located downhole. The drill collars 1015 may be used to add weight to the drill bit 1026. The drill collars 1015 also may stiffen the bottom hole assembly 1020 to allow the bottom hole assembly 1020 to transfer the added weight to the drill bit 1026, and in turn, assist the drill bit 1026 in penetrating the surface 1004 and subsurface formations 1014.

During drilling operations, a mud pump 1032 can pump drilling fluid (sometimes known by those of skill in the art as "drilling mud") from a mud pit 1034 through a hose 1036 into the drill pipe 1018 and down to the drill bit 1026. The drilling fluid can flow out from the drill bit 1026 and be returned to the surface 1004 through an annular area 1040 between the drill pipe 1018 and the sides of the borehole 1012. The drilling fluid may then be returned to the mud pit 1034, where such fluid is filtered. In some embodiments, the drilling fluid can be used to cool the drill bit 1026, as well as to provide lubrication for the drill bit 1026 during drilling operations. Additionally, the drilling fluid may be used to remove subsurface formation 1014 cuttings created by operating the drill bit 1026.

Various embodiments of techniques described herein measure fluid viscosity downhole in a well. A parameter associated with a response signal, obtained from driving a tube containing the fluid with an excitation signal for vibrating the tube, can be acquired while maintaining the tube in a vibrating mode. The parameter can be evaluated to measure the viscosity of the fluid. Such a parameter may be realized as an attenuation coefficient, a phase delay between a response signal and its corresponding drive signal, or other characteristic signal parameter that can be correlated to viscosity of a fluid in the tube. In various embodiments, the fluid viscosity may be measured in-situ downhole in the well.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of skill in the art upon studying the above description.

What is claimed is:

1. A method comprising:
    applying a modulated drive signal to a vibrating tube in a well, the vibrating tube containing fluid from the well, the modulated drive signal being a base signal at a first frequency modulated by another signal at a second frequency, the second frequency being lower than the first frequency;
    determining a change in a response signal sensed from the vibrating tube, the response signal generated in response to the modulated drive signal applied to the vibrating tube, the determined change in the response signal correlated to the modulated drive signal; and
    determining viscosity of the fluid from a calculated function of viscosity with respect to change in response signal, the calculated function generated from standard fluids with known viscosity.

2. The method of claim 1, wherein determining the viscosity of the fluid includes:
    determining a delta change as a difference in value between a base change and the determined change; and
    selecting a viscosity from a relationship of viscosity as a function of delta change evaluated at the determined delta change.

3. The method of claim 1, wherein determining the change includes determining a phase delay between the drive signal and the response signal from the vibrating tube in the well.

4. The method of claim 3, wherein the method includes using a tube of a fluid density sensor as the vibrating tube.

5. A method comprising:
    determining a change in a signal sensed from a vibrating tube in a well, the change in the signal relative to a drive signal applied to the vibrate the tube, the vibrating tube containing a fluid from the well, the signal generated in response to the drive signal applied to the vibrating tube such that change of the signal occurs as the vibrating tube is being driven; and
    determining the viscosity of the fluid using the determined change, wherein determining the change includes determining an attenuation in the signal sensed from the vibrating tube in the well.

6. The method of claim 5, wherein the method includes using a tube of a fluid density sensor as the vibrating tube.

7. The method of claim 5, wherein determining the viscosity of the fluid includes monitoring a rate of attenuation, determining a quality factor from the monitoring, and deriving the viscosity from the quality factor.

8. The method of claim 5, wherein the method includes driving the vibrating tube with a modulated drive signal without the fluid in the vibrating tube and determining a base attenuation coefficient.

9. The method of claim 5, wherein the method includes:
iteratively applying a modulated drive signal to the vibrating tube, the vibrating tube containing a different fluid in each iteration, each of the different fluids having a known viscosity;
determining an attenuation coefficient for each of the different fluids from applying the modulated drive signal in the respective iteration;
generating a delta attenuation coefficient for each of the different fluids, the delta attenuation coefficient for each fluid being a difference in value between a base attenuation coefficient and the respective determined attenuation coefficient;
storing each delta attenuation coefficient in a database such that each delta attenuation coefficient is correlated to its respective known viscosity in the database; and
determining the viscosity of the fluid using a relationship of viscosity as a function of delta attenuation coefficient from the correlation of delta attenuation coefficients with known viscosities in the database.

10. The method of claim 5, wherein the drive signal includes a base drive signal modulated by a square wave, the base drive signal having a frequency and the square wave having a low frequency relative to the frequency of the base drive signal.

11. A method comprising:
determining a phase delay between a response signal generated from a vibrating tube in a well and a drive signal applied to the vibrating tube, the vibrating tube containing a fluid from the well, the response signal generated in response to a drive signal applied to the vibrating tube such that the phase delay occurs as the vibrating tube is being driven, drive signal being a modulated drive signal generated as a base signal at a first frequency modulated by another signal at a second frequency, the second frequency being lower than the first frequency; and
determining viscosity of the fluid from a calculated function of viscosity with respect to change in phase delays the calculated function generated from standard fluids with known viscosity, the phase delays being between response signals and drive signals.

12. The method of claim 11, wherein the phase delay includes a phase delay between the modulated drive signal and a corresponding filtered response signal.

13. The method of claim 12, wherein the method includes using a tube of a fluid density sensor as the vibrating tube.

14. The method of claim 12, wherein the method includes:
iteratively applying the drive signal to the vibrating tube, the vibrating tube containing a different fluid in each iteration, each of the different fluids having a known viscosity;
determining a phase delay between the drive signal and a response signal responsive to the drive signal for each of the different fluids;
generating a delta phase delay for each of the different fluids, the delta phase delay for each fluid being a difference in value between a base phase delay and the respective determined phase delay;
storing each delta phase delay in a database such that each delta phase delay is correlated to its respective known viscosity; and
determining the viscosity of the fluid using a relationship of viscosity as a function of delta phase delay from correlation of delta phase delays with known viscosities in the database.

15. The method of claim 11, wherein determining the viscosity of the fluid using the determined phase delay includes:
determining a delta phase delay as a difference in value between a base phase delay and the determined phase delay; and
selecting a viscosity from a relationship of viscosity as a function of delta phase delay evaluated at the determined delta phase delay.

16. A method comprising:
determining a phase delay between a response signal generated from a vibrating tube in a well and a drive signal applied to the vibrating tube, the vibrating tube containing a fluid from the well, the response signal generated in response to a drive signal applied to the vibrating tube such that the phase delay occurs as the vibrating tube is being driven;
determining the viscosity of the fluid using the determined phase delay by selecting a viscosity from a predetermined relationship based on phase delays and standard fluids with known viscosity, wherein the phase delay includes a phase delay between a modulated drive signal and a corresponding filtered response signal or a phase delay between an un-modulated drive signal and a corresponding unfiltered response signal;
iteratively applying the drive signal to the vibrating tube, the vibrating tube containing a different fluid in each iteration, each of the different fluids having a known viscosity;
determining a phase delay between the drive signal and a response signal responsive to the drive signal for each of the different fluids;
generating a delta phase delay for each of the different fluids, the delta phase delay for each fluid being a difference in value between a base phase delay and the respective determined phase delay;
storing each delta phase delay in a database such that each delta phase delay is correlated to its respective known viscosity; and
determining the viscosity of the fluid using a relationship of viscosity as a function of delta phase delay from correlation of delta phase delays with known viscosities in the database, wherein the drive signal is a sinusoidal signal modulated by a lower frequency sinusoidal signal and the response signal is a filtered response to the sinusoidal signal modulated by the lower frequency sinusoidal signal.

17. A non-transitory machine-readable medium that stores instructions, which when performed by a machine, cause the machine to perform operations, the operations comprising:
applying a modulated drive signal to a vibrating tube in a well, the vibrating tube containing fluid from the well, the modulated drive signal being a base signal at a first frequency modulated by another signal at a second frequency, the second frequency being lower than the first frequency;
determining a change in a response signal sensed from the vibrating tube, the response signal generated in response to the modulated drive signal applied to the vibrating tube, the determined change in the response signal correlated to the modulated drive signal; and
determining viscosity of the fluid from a calculated function of viscosity with respect to change in response signal, the calculated function generated from standard fluids with known viscosity.

18. The non-transitory machine-readable medium of claim 17, wherein determining the viscosity of the fluid includes:
   determining a delta change as a difference in value between a base change and the determined change; and
   selecting a viscosity from a relationship of viscosity as a function of delta change evaluated at the determined delta change.

19. The non-transitory machine-readable medium of claim 17, wherein the instructions include using a tube of a fluid density sensor as the vibrating tube.

20. The non-transitory machine-readable medium of claim 17, wherein the instruction, which when performed by a machine, cause the machine to perform operations, the operations including:
   prior to applying the modulated drive signal to the vibrating tube in the well, generating the predetermined relationship between change in response and standard fluids with known viscosity by:
      iteratively applying a modulated drive signal to the vibrating tube, the vibrating tube containing a different fluid in each iteration, each of the different fluids having a known viscosity;
   determining a change in a response signal for each of the different fluids from applying the modulated drive signal in the respective iteration;
   generating a delta change for each of the different fluids, the delta change for each fluid being a difference in value between a base change value and the determined change for the respective fluid; and
   storing each delta change in a database such that each delta change is correlated to its respective known viscosity in the database.

21. A non-transitory machine-readable medium that stores instructions, which when performed by a machine, cause the machine to perform operations, the operations comprising:
   applying a modulated drive signal to a vibrating tube in a well, the vibrating tube containing a fluid from the well;
   determining a change in a response signal sensed from the vibrating tube, the response signal generated in response to the modulated drive signal applied to the vibrating tube, the determined change in the response signal correlated to the modulated drive signal; and
   determining viscosity of the fluid by selecting a viscosity from a predetermined relationship between change in response and standard fluids with known viscosity, wherein the modulated drive signal includes a base signal modulated by a square wave having a low frequency relative to the frequency of the base signal for determining an attenuation or the modulated drive signal includes a sinusoidal signal having a frequency modulated by a lower frequency sinusoidal signal for determining a phase delay.

22. An apparatus comprising:
   a sensor device to measure viscosity of a fluid in a well, the sensor device including:
      a tube to contain fluid extracted from the well;
      a drive source to generate a modulated drive signal to vibrate the tube, the modulated drive signal being a base signal at a first frequency modulated by another signal at a second frequency, the second frequency being lower than the first frequency;
      a sensing circuit to generate a response signal representing a response of the tube to the modulated drive signal; and
      an analysis unit to determine a change in the response signal, the response signal generated in response to the modulated drive signal applied to the tube, the determined change in the response signal correlated to the modulated drive signal, the analysis unit to determine the viscosity of the fluid from a calculated function of viscosity with respect to change in response signal, the calculated function generated from standard fluids with known viscosity.

23. The apparatus of claim 22, wherein the sensor device includes a fluid density sensor to provide the tube vibrated by the drive signal.

24. The apparatus of claim 22, wherein the analysis unit includes a low-pass filter to filter the response signal.

25. The apparatus of claim 22, wherein the analysis unit includes a database containing delta attenuation coefficients correlated to known viscosities or delta phase delays correlated to known viscosities.

26. The apparatus of claim 22, wherein the analysis unit includes a machine-readable medium that stores instructions, which when performed by the analysis unit, cause the apparatus to perform operations, the operations comprising:
   determining the change in the response signal sensed from vibrating the tube, the determined change in the response signal correlated to the modulated drive signal; and
   determining
   determining the viscosity of the fluid by selecting a viscosity from the predetermined relationship between change in response and standard fluids with known viscosity.

27. The apparatus of claim 26, wherein determining the viscosity of the fluid includes;
   determining a delta change as a difference in value between a base change and the determined change; and
   selecting a viscosity from a relationship of viscosity as a function of the delta change evaluated at the determined change.

28. An apparatus comprising:
   a sensor device to measure viscosity of a fluid in a well, the sensor device including:
      a tube to contain fluid extracted from the well;
      a drive source to generate a drive signal to vibrate the tube, wherein the drive source includes a circuit to generate a base signal modulated by a square wave having a low frequency relative to the frequency of the base signal;
      a sensing circuit to generate a response signal representing a response of the tube to the drive signal, and an analysis unit to determine a parameter of the response signal, the response signal generated in response to the drive signal applied to the tube such that acquisition of the parameter occurs as the vibrating tube is being driven, the analysis unit to determine the viscosity of the fluid using the parameter.

29. An apparatus comprising:
   a sensor device to measure viscosity of a fluid in a well, the sensor device including:
      a tube to contain fluid extracted from the well;
      a drive source to generate a drive signal to vibrate the tube, wherein the drive source includes a circuit to generate a sinusoidal signal having a frequency modulated by a lower frequency sinusoidal signal;
      a sensing circuit to generate a response signal representing a response of the tube to the drive signal, and an analysis unit to determine a parameter of the response signal, the response signal generated in response to the drive signal applied to the tube such that acquisition of the parameter occurs as the vibrating tube is being driven, the analysis unit to determine the viscosity of the fluid using the parameter.

* * * * *